United States Patent [19]

Etienne et al.

[11] Patent Number: 4,755,385

[45] Date of Patent: Jul. 5, 1988

[54] ORAL PHARMACEUTICAL PREPARATIONS CONTAINING 9-DEOXO-11-DEOXY-9,11-[IMINO[2-(2-METHOXYETHOXY)-ETHYLIDENE]-OXY]-(9S)-ERYTHROMYCIN

[75] Inventors: Alain Etienne, St. Médard en Jalles, France; Peter Gruber; Ulrich Busch, both of Biberach, Fed. Rep. of Germany

[73] Assignee: Dr. Karl Thomae, GmbH, Biberach, Fed. Rep. of Germany

[21] Appl. No.: 882,999

[22] Filed: Jul. 8, 1986

[30] Foreign Application Priority Data

Jul. 10, 1985 [DE] Fed. Rep. of Germany ....... 3524572

[51] Int. Cl.$^4$ .................... A61K 9/28; A61K 9/22; A61K 9/26
[52] U.S. Cl. .................... 424/154; 424/156; 424/157; 424/465; 424/474; 424/489; 424/490; 514/29
[58] Field of Search ............... 514/29; 924/154, 156, 924/157, 465, 474, 489, 490

[56] References Cited

U.S. PATENT DOCUMENTS

| | | | |
|---|---|---|---|
| 3,081,233 | 3/1963 | Enz et al. .............................. | 514/29 |
| 3,784,683 | 1/1974 | Prillig et al. ......................... | 424/469 |
| 3,865,935 | 2/1975 | Amann .................................. | 514/29 |
| 3,891,755 | 6/1975 | Mehta ................................... | 514/29 |
| 4,101,651 | 7/1978 | Kobayashi et al. ................... | 424/35 |
| 4,127,647 | 11/1978 | Sato et al. ............................ | 514/29 |
| 4,289,751 | 9/1981 | Windheuser .......................... | 514/29 |
| 4,340,582 | 7/1982 | Kriesel et al. ........................ | 514/29 |

*Primary Examiner*—Shep K. Rose
*Attorney, Agent, or Firm*—David E. Frankhouser; Alan R. Stempel; Mary-Ellen M. Timbers

[57] ABSTRACT

There is described a solid pharmaceutical preparation for oral administration which produces high and long-lasting blood and tissue levels, containing 9-deoxo-11-deoxy-9,11-[imino[2-(2-methoxyethoxy)-ethylidene]oxy]-(9S)-erythromycin as active substance, in which the active substance must be intimately mixed with a basic excipient in a ratio of 1 mol of active substance to at least 2 gram-equivalents of basic excipient, and the preparations are coated with a gastric juice-resistant lacquer which is soluble in a pH range of between 5.5 and 6.8, and processes for preparing them. The solid pharmaceutical preparations include tablets, pellets or granules and a syrup can be produced from the latter.

7 Claims, 1 Drawing Sheet

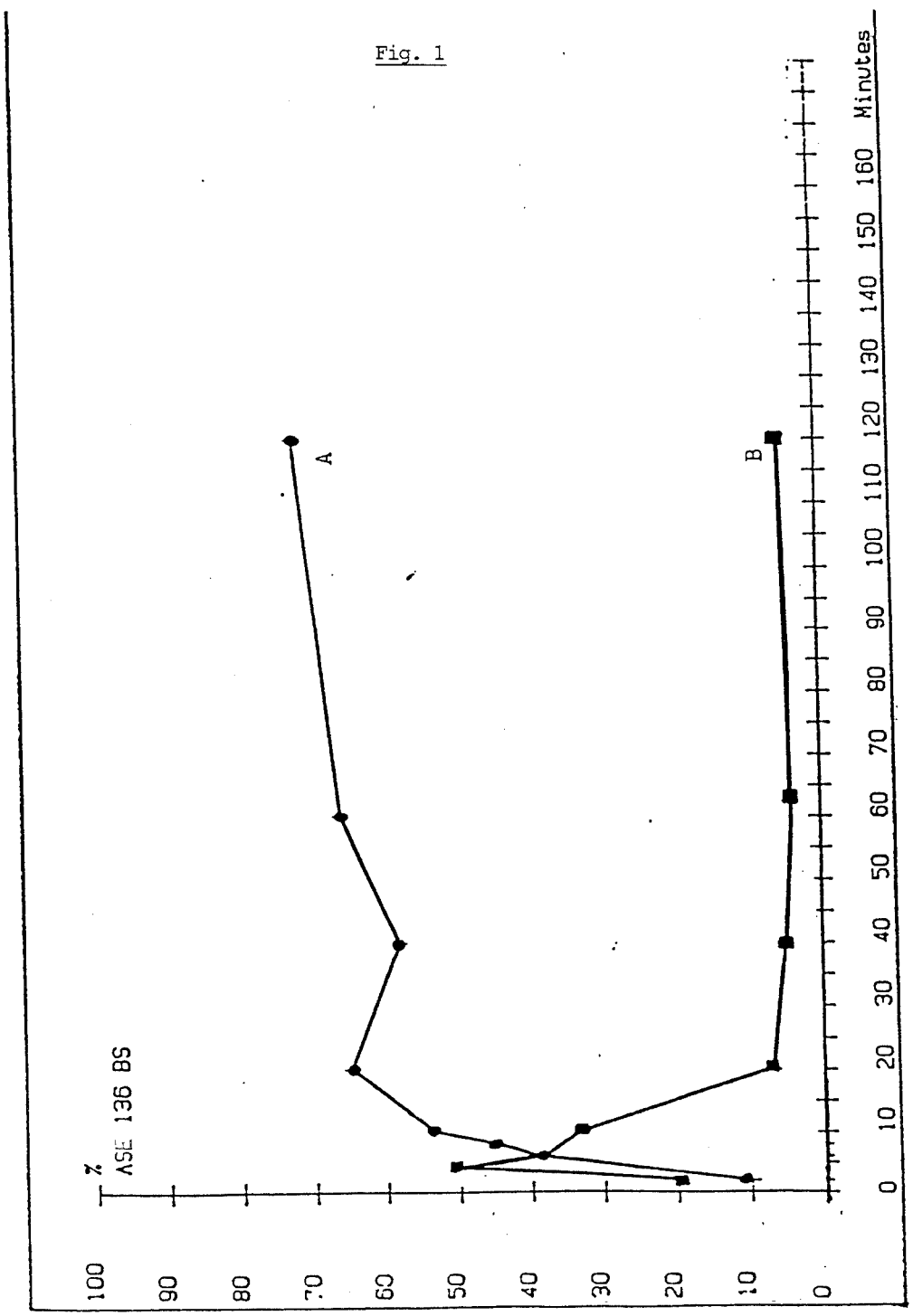

ORAL PHARMACEUTICAL PREPARATIONS CONTAINING 9-DEOXO-11-DEOXY-9,11-[IMINO[2-(2-METHOXYETHOXY)-ETHYLIDENE]-OXY]-(9S)-ERYTHROMYCIN

The invention relates to new oral solid pharmaceutical preparations containing 9-deoxo-11-deoxy-9,11-[imino[2-(2-methoxyethoxy)-ethylidene]oxy]-(9S)-erythromycin, hereinafter referred to as AS-E 136, and processes for the preparation thereof.

In DE-A1-2,515,075 (cf. also British Pat. No. 1 520 963) AS-E 136 is described as a substance with particularly good antibacterial activity. This is achieved particularly when this substance is administered in dissolved form circumventing the gastrointestinal tract, e.g., by the intravenous route. AS-E 136 has considerable advantages over other macrolide antibiotics since it need only be administered once a day in a total dosage of up to 500 mg. It is distinguished from other antibiotics of the same structural type, e.g., erythromycin, by the exceptionally high and long-lasting tissue levels.

However, preparations for oral administration containing AS-E 136 produced in the usual way result in very low and generally fluctuating tissue levels after administration and therefore these preparations have hitherto been found to be unsuitable for the administration of this active substance. There was an urgent need to discover and develop pharmaceutical preparations for oral administration containing AS-E 136 which did not have these disadvantages.

AS-E 136 is characterized by marked sensitivity to acidic media and the active substance is usually destroyed in a short time by the action of gastric juices (pH 1.0 to 2.0), like other many macrolide antibiotics such as erythromycin. The main decomposition product of AS-E 136 is erythromycylamine, which does indeed develop an antibacterial activity but when administered orally in man is resorbed to such a small degree that microbiologically effective blood levels can only be built up with this substance by administering very high doses or cannot be built up at all. This can be demonstrated by the values obtained for the areas under the plasma level curve (AUC—area under the curve).

Table 1 shows the AUC values after the administration of erythromycylamine.

TABLE 1

AUC values (rounded off) of plasma levels after oral administration in tablet form to 7 subjects.

| Subject | AUC up to 24 hours post application (mcg/ml × h) × 1000 |
| --- | --- |
| 1 | 700 |
| 2 | 300 |
| 3 | 500 |
| 4 | 500 |
| 5 | 550 |
| 6 | 100 |
| 7 | 250 |

Even at pH values of around 5.5 at which erythromycin is chemically stable long enough to be resorbed, AS-E 136 retains its susceptibility to hydrolysis unchanged. Only at pH values of around or above 7.0 does AS-E 136 gain stability, as shown in the following Tables 2 and 3:

TABLE 2

| pH value | % intact erythromycin base | |
| --- | --- | --- |
| | after 30 min. | after 60 min. |
| 1.3 | 30 | 10 |
| 4.5 | 55 | 50 |
| 5.5 | 100 | 85 |

TABLE 3

| pH value | % intact substance AS-E 136 after 30 minutes |
| --- | --- |
| 1.0 | 10 |
| 6.0 | 20 |
| 6.5 | 20 |
| 7.0 | 50 |
| 7.5 | 80 |
| 8.0 | 95 |

Nor can AS-E 136, optionally together with other adjuvants such as carriers and disintegrants, simply be coated with a lacquer resistant to gastric juices which releases the active substance only at pH levels above 7.0, since there is no such pH range in the gastrointestinal tract where resorption is supposed to take place. This is clear from the following findings: the average pH levels of the human intestine range between 5.0 and 7.0, namely 5.0 in the uppermost section of the intestine (duodenum) and 7.0 in the lowest section (the colon). It is also known that the extent of resorption in lower sections of the intestine is greatly restricted. This applies particularly to large molecules such as the macrolide AS-E 136. It would not be difficult, for example, to develop a reliable pharmaceutical form for an active substance such as erythromycin which is susceptible to gastric juices since the active substance is sufficiently stable in the upper section of the intestine (pH about 5 to 5.5). In this case, it is well known to compress the active substance to form a tablet, e.g. with suitable excipients, and coat this tablet with so-called gastric juice-resistant lacquers such as cellulose acetate phthalate or hydroxypropylmethylcellulose phthalate. After leaving the stomach, this lacquer dissolves in the intestinal juices, the active substance is dissolved and resorbed. This known principle cannot be applied to AS-E 136 since the active substance only acquires adequate stability at a pH of 7.5, as shown in Table 3. However, this pH is not generally attained in the intestines or is only attained in the region of the colon transcendens or descendens. At this point, however, the pharmaceutical preparation is enclosed in the thickened feces and the extent of resorption is only very slight.

The complex dependency of AS-E 136 resorption on the pH profile in the individual sections of the intestine and the extent of resorption in the lower intestinal areas, decreasing for other reasons, can be precisely demonstrated with AS-E preparations which release the active substance in various parts of the intestines as a result of the gastric juice-resistant lacquer used (see Table 4).

TABLE 4

AUC values (rounded off) of plasma levels of various charges with release of active substance at different pH levels

| Charge No. | Release at pH | AUC values 0–24 hours (mcg/ml × h) × 1000 | |
| --- | --- | --- | --- |
| | | min. | max. |
| ZP 234/12 | 5.0 | 1.0 | 56.0 |
| ZP 234/13 | 6.2–6.7 | 650.0 | 1650.0 |

TABLE 4-continued

AUC values (rounded off) of plasma levels of various charges with release of active substance at different pH levels

| Charge No. | Release at pH | AUC values 0–24 hours (mcg/ml × h) × 1000 min. | max. |
|---|---|---|---|
| ZP 234/14 | 7.0–7.4 | 130.0 | 390.0 |

The charge ZP 234/12 consists of 23.52% of starter cores consisting of 70% sucrose and 30% powdered corn starch, 46.37% active substance, 15.65% talc, 5.65% polyvinylpyrrolidone, 7.05% hydroxypropylmethylcellulose phthalate and 1.96% castor oil. The charge ZP 234/13 consists of 24.91% of starter cores having the same composition, 49.54% of active substance, 11.52% of talc, 6.05% of polyvinylpyrrolidone, 4.36% of Eudragit S, 1.09% of Eudragit L, 1.64% of castor oil, 0.91% of magnesium stearate. The charge ZP 234/14 consists of 23.5% of starter cores having the same composition, 46.74% of active substance, 11.60% of talc, 5.71% of polyvinylpyrrolidone, 7.89% of Eudragit S, 1.03% of Eudragit L, 2.67% of castor oil, 0.86% of magnesium stearate (the percentages are given as % by weight, the active substance is AS-E 136).

The above Table shows that pellets coated with a lacquer which permits release of the active substance at pH 5.0 (pH range in the duodenum at the exit from the stomach) show virtually no blood levels with antimicrobial activity. If the same pellets are coated with a coating permitting release of the active substance at a pH of between 6.2 and 6.7 (the pH range in the lower duodenum down to the ileum), only fluctuating and low blood levels are achieved, but if these pellets are coated with a film which allows the active substance to be released only at a pH of 7.0 to 7.4, a significant fall in the blood levels is again observed. Thus, if a lacquer which releases the active substance in an intestinal range at pH 5.0 is used, virtually no blood levels are achieved, i.e. the active substance is destroyed more quickly than it is absorbed. If, on the other hand, the active substance is released in a pH range in which it is more stable (pH 7.0 to 7.4), once again virtually no blood levels are achieved since there is virtually no resorption in this section of the intestines (the colon). If the active substance is released by the use of a lacquer which releases it in a section of intestines with pH values of between 6.2 and 6.7, only very modest blood level values are achieved since the speed of decomposition of the active substance is greater than the speed of its resorption, as shown in Table 3. To sum up, it can be said that it is impossible to produce suitable solid pharmaceutical preparations of AS-E 136 with reliable resorption using the various gastric juice-resistant lacquers available.

It has now been found that solid pharmaceutical preparations suitable for oral administration which contain AS-E 136 and guarantee high and scarcely fluctuating blood level values can be produced by intimately mixing the finely divided active substance with a basic excipient in a ratio of 1 mol of active substance to at least 2 gram equivalents of basic excipient. The mixture may even be granulated and compressed to form tablets, optionally after the addition of other excipients such as disintegrants, binders and lubricants, or the mixture may be pelleted, optionally after the addition of adhesives, e.g. by applying it to sugar pellets. Furthermore, the mixture may be compacted into briquettes, e.g. using a roller compactor, in order to prepare granulates, optionally after the addition of further excipients. The mixture may also be suspended in a melt of fats such as stearyl alcohols or polyethylene glycols and spray-hardened in a cooling tower to form small uniform particles. The preparations such as tablets, pellets and granules obtained by these processes are then coated with a gastric juice-resistant lacquer which is soluble in a pH range of between 5.5 and 6.8 or which releases the active substance at a pH of between 5.5 and 6.8, preferably between 6.0 and 6.4.

An example of a product according to the invention is shown in Table 5 which lists the AUC values of plasma levels after the administration of a mixture of 100 mg of AS-E 136 and 100 mg of magnesium carbonate according to Example 1.

TABLE 5

AUC values (rounded off) of plasma levels after oral administration of 500 mg of AS-E 136 in tablet form to 12 subjects

| Subject | AUC up to 24 hours p.a. (mcg/ml × h) × 1000 |
|---|---|
| 1 | 2 600 |
| 2 | 1 900 |
| 3 | 3 800 |
| 4 | 1 900 |
| 5 | 2 100 |
| 6 | 2 800 |
| 7 | 1 500 |
| 8 | 1 000 |
| 9 | 2 800 |
| 10 | 2 600 |
| 11 | 2 600 |
| 12 | 3 800 |

The basic excipients used may be, either on their own or combined with one another, oxides, hydroxides or carbonates of magnesium or calcium, such as magnesium oxide, magnesium hydroxide, magnesium carbonate, magnesium hydrogen carbonate, calcium hydroxide, calcium carbonate, magnesium aluminium hydroxide, magnesium aluminate or carbonates, hydrogen carbonates or hydroxides of sodium or potassium such as sodium carbonate, sodium hydrogen carbonate, potassium carbonate, potassium hydrogen carbonate, sodium or potassium hydroxide, but also strongly basic alkali metal salts such as trisodium phosphate. The preferred basic excipients are magnesium carbonate, magnesium oxide and sodium carbonate.

The active substance and the basic excipient are mixed together in a ratio of at least 1 gram-mol of active substance to 2 gram-equivalents of basic excipient. The upper limit of basic excipients will be determined by the size of the resulting pharmaceutical preparations and/or the physiological tolerance to the basic excipient. A pharmaceutical preparation of large volume is difficult to administer. Generally, the upper limit of the basic excipient is 200 gram-equivalents. The preferred ratio of active substance to basic excipient is 1 gram-mol of active substance to 15 to 50 gram-equivalents of basic excipient.

The gastric juice-resistant lacquers used are preferably hydroxypropylmethylcellulose phthalate, copolymers of methacrylic acid and methyl methacrylate (Eudragit L ® and Eudragit S ®), cellulose acetate phthalate, mixtures of these lacquers and also other lacquers which dissolve in a pH range of from 5.5 to 6.8. The quantity of lacquer used is such that the preparations coated with the lacquer in question are resistant to gastric juices for a period of between 30 minutes and 2 hours; small preparations, e.g. granulates and pellets, should be resistant to gastric juices for at least 30 minutes while larger tablets should be resistant for 2 hours. Resistant to gastric juices means that these preparations should release virtually no active substance within the periods specified when tested in artificial gastric juices.

The addition of a disintegrant will ensure rapid release of the active substance provided with the basic excipient, particularly in large-volume pharmaceutical preparations, and will thus ensure fast resorption and activity. The disintegrant will ensure rapid disintegration into particles, e.g. in the case of tablets. This increases the surface area of the pharmaceutical mass, while the basic excipient will protect the acid-susceptible active substance for a sufficient period of time to allow the active substance to be resorbed. The quantity of disintegrant is calculated, as a function of its activity, so that the core of the pharmaceutical preparation, e.g. the tablet core, will disintegrate within 1 hour, preferably within 30 minutes. Suitable disintegrants are the excipients conventionally used such as starch, Croscarmelose sodium (AC-DT-SOL ®), sodium starch glycolate or Crospovidone, on their own or combined with one another.

It is important with all the pharmaceutical preparations according to the invention that the active substance which is susceptible at pH levels of up to 7 is always intimately connected with the basic excipient. This is achieved by intimately mixing the two substances and, for example, compressing the mixture to form tablets, optionally after the addition of further excipients. These further excipients can be, in particular, the disintegrants described above and also other conventional additives such as polyvinylpyrrolidone or lubricants such as magnesium stearate. The material to be made into tablets is moistened and granulated and the dried granules are compressed into tablets. The resulting tablet is coated according to the invention with one of the above mentioned gastric juice-resistant lacquers, for example by spraying with a suitable lacquer solution.

Another possibility is to provide the intimate mixture of active substance and basic excipient with an adhesive substance such as polyvinylpyrrolidone and to "stick" this mixture onto pellet starter cores. Rounded sugar pellets can be used, for example, as the pellet starter cores; the suspension of active substance, basic excipient and adhesive substance is sprayed onto these pellet starter cores. The intimate mixture mentioned above can also be pelleted by a number of other methods known per se.

If, on the other hand, granules of active substance are to be produced, an intimate mixture of active substance, basic excipient and other additives, e.g. adhesive substances such as polyvinylpyrrolidone, can be made into briquettes in the moistened state using a roller compactor. The coarse particles thus produced are broken up, the suitably sized fraction is screened off and the rest is recycled into the roller compactor.

If particularly small and uniformly large particles are to be produced, e.g. for the preparation of pharmaceutical suspensions, in which the particles should preferably have a diameter of from 0.2 to 0.5 mm, spray hardening is preferably used. In this case, the active substance together with the basic excipient is suspended in a melt and this melt is sprayed in a cooling tower. Suitable melts include, for example, fats or fatty alcohols with a sharp melting point, e.g. stearyl alcohol, and also other materials with similar physical properties, e.g. polyethyleneglycols.

All the particles obtained by these processes are subsequently coated with a gastric juice-resistant lacquer which dissolves in a pH range of between 5.5 and 6.8.

After the gastric juice-resistant lacquer has dissolved in the intestinal tract, a basic microsphere with a higher pH than its surroundings forms around the active substance and stabilizes it in this range. The particles with their microspheres move preferentially along the lining of the intestines. As a result of the consequently short diffusion route, it is possible for the active substance to be resorbed with substantially no decomposition, one point in favor of this active substance being that it has a relatively high resorption rate compared with erythromycylamine, its decomposition product.

FIG. 1 shows the profile of dissolution of a tablet produced according to Example 1 in artificial intestinal juices at pH 6.0 by comparison with a tablet without the basic excipient. The tablet cores are placed in a USPXX apparatus and stirred with the paddle at 100 rpm. In the FIGURE, the ordinates show the non-decomposed AS-E 136 as a function of time. The curve A corresponds to the tablet produced in Example 1, while curve B corresponds to the comparison tablet without the basic excipients added to it.

The following Examples illustrate the invention:

EXAMPLE 1

Composition of a tablet:

| AS-E 136 | 100 mg | (1) |
|---|---|---|
| Magnesium carbonate | 100 mg | (2) |
| Polyvinylpyrrolidone, cross-linked | 44.5 mg | (3) |
| Polyvinylpyrrolidone | 5.0 mg | (4) |
| Magnesium stearate | 1.0 mg | (5) |
| Cellulose acetate phthalate | 24.8 mg | (6) |
| Dibutylphthalate | 1.2 mg | (7) |
| | 276.5 mg | |

The active substance (1), basic excipient (2) and disintegrant (3) are mixed together in the proportions specified and moistened with the adhesive (4), dissolved in isopropanol, then granulated and dried. After the lubricant (5) has been added the material is compressed to form tablets which are coated by spraying with a mixture of the lacquer component (6) and (7) dissolved in ethanol/methylene chloride.

The gastric juice-resistant tablet is tested in a USPXX release apparatus (paddle method, 100 rpm, 37° C.). The same preparation is stirred into the individual media one after another.

| Time | Medium | pH value | release in % |
|---|---|---|---|
| 1 hour | artif. gastric juice | 1.2 | 0 |
| 1 hour | artif. intestinal juice | 4.5 | 0 |
| 15 min. | artif. intestinal juice | 6.0 | 21.1 |
| 30 min. | artif. intestinal juice | 6.0 | 98.4 |

EXAMPLE 2

Composition of a tablet:

| AS-E 136 | 100 mg | (1) |
|---|---|---|
| Magnesium carbonate | 250 mg | (2) |
| Disintegrant starch | 44.5 mg | (3) |

| -continued | | |
|---|---|---|
| Polyvinylpyrrolidone | 8.0 mg | (4) |
| Magnesium stearate | 1.0 mg | (5) |
| Cellulose acetate phthalate | 27.7 mg | (6) |
| Dibutylphthalate | 1.4 mg | (7) |
| | 432.6 mg | |

Tablets of this composition are prepared as described in Example 1. The release values as a function of time and pH are as follows:

| Time | Medium | pH value | release in % |
|---|---|---|---|
| 1 hour | artif. gastric juice | 1.2 | 0 |
| 1 hour | artif. intestinal juice | 4.5 | 0 |
| 15 min. | artif. intestinal juice | 6.0 | 10.9 |
| 30 min. | artif. intestinal juice | 6.0 | 99.2 |

EXAMPLE 3

Composition of a tablet:

| AS-E 136 | 100 mg | (1) |
|---|---|---|
| Magnesium oxide | 175 mg | (2) |
| Disintegrant starch | 65 mg | (3) |
| Microcrystalline cellulose | 110 mg | (4) |
| Polyvinylpyrrolidone | 2 mg | (4) |
| Magnesium stearate | 2.5 mg | (5) |
| Cellulose acetate phthalate | 31.8 mg | (6) |
| Dibutylphthalate | 1.6 mg | (7) |
| | 482.9 mg | |

Gastric juice-resistant tablets having this composition are prepared as described in Example 1. The release values as a function of time and pH are as follows:

| Time | Medium | pH value | release in % |
|---|---|---|---|
| 1 hour | artif. gastric juice | 1.2 | 0 |
| 1 hour | artif. intestinal juice | 4.5 | 0 |
| 15 min. | artif. intestinal juice | 6.0 | 0 |
| 20 min. | artif. intestinal juice | 6.0 | 77.9 |
| 30 min. | artif. intestinal juice | 6.0 | 99.4 |

EXAMPLE 4

Composition of a tablet:

| AS-E 136 | 125 mg | (1) |
|---|---|---|
| Aluminium hydroxide | 20 mg | (2) |
| Calcium hydroxide | 10 mg | (2) |
| Disintegrant starch | 35 mg | (3) |
| Polyvinylpyrrolidone | 6 mg | (4) |
| Magnesium stearate | 1 mg | (5) |
| Copolymer of methacrylate ester (Eudragit L) | 18 mg | (6) |
| Triacetin | 2 mg | (7) |
| | 217 mg | |

Gastric juice-resistant tablets having this composition are prepared as described in Example 1. The release values as a function of time and pH are as follows:

| Time | Medium | pH value | release in % |
|---|---|---|---|
| 2 hours | artif. gastric juice | 1.2 | 0 |
| 15 min. | artif. intestinal juice | 6.2 | 32 |
| 30 min. | artif. intestinal juice | 6.2 | 96.4 |

EXAMPLE 5

Composition of a tablet:

| AS-E 136 | 125 mg | (1) |
|---|---|---|
| Sodium carbonate | 125 mg | (2) |
| Disintegrant starch | 56 mg | (3) |
| Polyvinylpyrrolidone | 6 mg | (4) |
| Magnesium stearate | 3 mg | (5) |
| Cellulose acetate phthalate | 30 mg | (6) |
| Dibutylphthalate | 1.6 mg | (7) |
| | 346.6 mg | |

Gastric juice-resistant tablets having this composition are prepared as described in Example 1. The release values as a function of time and pH are as follows:

| Time | Medium | pH value | release in % |
|---|---|---|---|
| 2 hours | artif. gastric juice | 1.2 | 0 |
| 15 min. | artif. intestinal juice | 6.0 | 24.3 |
| 30 min. | artif. intestinal juice | 6.0 | 98.2 |

EXAMPLE 6

Pellets containing AS-E 136:

| AS-E 136 | 2.8 kg | (1) |
|---|---|---|
| Calcium hydroxide | 4.2 kg | (2) |
| Disintegrant starch | 1.2 kg | (3) |
| Methylcellulose | 0.4 kg | (4) |
| Polyethylene glycol 6000 | 1.4 kg | (5) |
| Hydroxypropylmethyl-cellulose phthalate | 0.8 kg | (6) |
| Castor oil | 0.2 kg | (7) |
| Talc | 0.4 kg | (8) |

Components (1) to (5) are mixed together and moistened with water. The moistened screened mass is extruded through a screen with a mesh size of 0.8 mm. The extruded strips are rounded in a Merumerizer. Components (6) to (8) are dissolved or suspended in isopropanol/acetone 6:3/v:v and the solution is sprayed onto the dried pellets. The release values as a function of time and pH are as follows:

| Time | Medium | pH value | release in % |
|---|---|---|---|
| 2 hours | artif. gastric juice | 1.2 | 0 |
| 15 min. | artif. intestinal juice | 6.4 | 47.5 |
| 30 min. | artif. intestinal juice | 6.4 | 96.9 |

EXAMPLE 7

AS-E 136 granulate:

| AS-E 136 | 2.72 kg | (1) |
|---|---|---|
| Magnesium hydrogen carbonate | 2.72 kg | (2) |
| Disintegrant starch | 0.95 kg | (3) |
| Polyvinylpyrrolidone | 0.14 kg | (4) |
| Cellulose acetate phthalate | 3.38 kg | (5) |
| Dibutylphthalate | 0.09 kg | (6) |

Components (1) to (4) are mixed together and made into briquettes by means of a roller compactor. This material is broken up and the fraction measuring 0.2 to 0.45 mm is screened off. The fine fraction and coarse fraction are re-compacted and broken up. Particles measuring 0.2 to 0.45 mm are coated with components (5) and (6), dissolved in ethanol/methylene chloride 1:1/v:v. The release values as a function of time and pH are as follows:

| Time | Medium | pH value | release in % |
|------|--------|----------|--------------|
| 1 hour | artif. gastric juice | 1.2 | 3 |
| 15 min. | artif. intestinal juice | 6.0 | 69 |
| 30 min. | artif. intestinal juice | 6.0 | 99.3 |

Suspension from this granulate:

The coated particles are then mixed with the additives specified and suspended in water. The suspension contains, per 20 ml:

| | | |
|---|---|---|
| Gastric juice-resistant AS-E 136 granulate | 919.2 mg | |
| Citric acid | 150.0 mg | |
| Sucrose | 5000.0 mg | |
| Sodium saccharinate | 5.0 mg | |
| Orange flavoring | 60.0 mg | |
| Xanthan gum | 125.0 mg | |

EXAMPLE 8

AS-E 136 pellets:

| | | |
|---|---|---|
| AS-E 136 | 1.8 kg | (1) |
| Trisodium phosphate | 1.2 kg | (2) |
| Stearyl alcohol | 6.0 kg | (3) |
| Lactose | 0.5 kg | (4) |
| Copolymer of methacrylate ester (Eudragit S) | 2.2 kg | (5) |
| Hydroxypropylmethyl-cellulose phthalate (HP 55) | 0.8 kg | (6) |
| Talc | 3.0 kg | (7) |

The stearyl alcohol (3) is melted at 75° C. and components (1), (2) and (4) are vigorously suspended therein. The suspension is sprayed in a cooling tower via a single substance phase. The spray-hardened particles (more than 80% measuring between 0.2 and 0.5 mm in diameter) are carefully sprayed with lacquer components (5), (6) and (7), dissolved or suspended in isopropanol/acetone (1:1,v:v), in order to prevent the fine particles from sticking together as fat as possible. The release values as a function of time and pH are as follows:

| Time | Medium | pH value | release in % |
|------|--------|----------|--------------|
| 30 min. | artif. gastric juice | 1.2 | 3 |
| 15 min. | artif. intestinal juice | 6.5 | 74 |
| 30 min. | artif. intestinal juice | 6.5 | 99.1 |

What is claimed is:

1. A solid pharmaceutical preparation for oral administration comprising 9-deoxo-11-deoxy-9,11-[imino[2-(2-methoxyethoxy)-ethylidene]-oxy]-(9S)-erythromycin intimately mixed with a basic excipient in a ratio of 1 mol of 9-deoxo-11-deoxy-9,11-[imino[2-(2-methoxyethoxy)-ethylidene]-oxy]-(9S)-erythromycin to at least 2 gram-equivalents of basic excipient and an effective amount of a disintegrant, to insure disintegration, fast resorption and action, and coated with a gastric juice-resistant lacquer which releases the 9-deoxo-11-deoxy-9,11-[imino[2-(2-methoxyethoxy)-ethylidene]-oxy]-(9S)-erythromycin for resorption in the uppermost sections of the intestines, where blood levels are achieved, other than the colon, in a pH range between 5.5 and 6.8.

2. The solid pharmaceutical preparation of claim 1, in which the intimate mixture of 9-deoxo-11-deoxy-9,11-[imino[2-(2-methoxyethoxy)-ethylidene]-oxy]-(9S)-erythromycin, said basic excipient and said disintegrant is compressed to form a tablet which is coated with said gastric juice-resistant lacquer.

3. The solid pharmaceutical preparation of claim 1 in which the intimate mixture of 9-deoxo-11-deoxy-9,11-[imino[2-(2-methoxyethoxy)-ethylidene]oxy]-(9S)-erythromycin, said basic excipient and said disintegrant is present in pellet form, which pellets are coated with said gastric juice-resistant lacquer.

4. The solid pharmaceutical preparation of claim 1 in which the intimate mixture of 9-deoxo-11-deoxy-9,11-[imino[2-(2-methoxyethoxy)-ethylidene]-oxy]-(9S)-erythromycin, said basic excipient and said disintegrant is present in granulate form which granules are coated with said gastric juice-resistant lacquer.

5. The solid pharmaceutical preparation of claim 1 in which the intimate mixture of 9-deoxo-11-deoxy-9,11-[imino[2-(2-methoxyethoxy)-ethylidene]-oxy]-(9S)-erythromycin, said basic excipient and said disintegrant is present in the form of spray-hardened spheroid particles, which particles are coated with said gastric juice-resistant lacquer.

6. The solid pharmaceutical preparation of claim 1 in which the gastric juice-resistant lacquer which releases the 9-deoxo-11-deoxy-9,11-[imino[2-(2-methoxyethoxy)-ethylidene]-oxy]-(9S)-erythromycin in a pH range of between 6.0 and 6.4.

7. The solid pharmaceutical preparation of claim 1 in which said basic excipient is magnesium oxide, magnesium carbonate, magnesium hydrogen carbonate, magnesium hydroxide, calcium hydroxide, calcium carbonate, magnesium aluminium hydroxide, magnesium aluminate, sodium carbonate, sodium hydrogen carbonate, potassium carbonate, potassium hydrogen carbonate, sodium hydroxide, postassium hydroxide, trisodium phosphate, or mixtures thereof.

* * * * *